United States Patent
Pfeiler et al.

[11] Patent Number: 5,558,640
[45] Date of Patent: Sep. 24, 1996

[54] SYSTEM FOR INFUSION OF MEDICINE INTO THE BODY OF A PATIENT

[75] Inventors: Manfred Pfeiler, Erlangen; Konrad Mund, Uttenreuth; Walter Preidel, Erlangen, all of Germany; Goesta Sjoeholm, Ekeroe, Sweden

[73] Assignee: Siemens Aktiengesellschaft, Munich, Germany

[21] Appl. No.: 400,953

[22] Filed: Mar. 8, 1995

[30]   Foreign Application Priority Data

Mar. 17, 1994 [EP] European Pat. Off. ............. 94104243

[51] Int. Cl.$^6$ ........................ A61M 31/00; A61K 9/22; A61N 1/18
[52] U.S. Cl. ........................ 604/67; 604/891.1; 607/32
[58] Field of Search .................... 604/65, 66, 67, 604/50, 31, 890.1, 891.1; 607/32; 128/DIG. 12, DIG. 13, 631, 632, 635

[56]   References Cited

U.S. PATENT DOCUMENTS

| | | | |
|---|---|---|---|
| 4,146,029 | 3/1979 | Ellinwood, Jr. | 128/903 |
| 4,494,950 | 1/1985 | Fischell . | |
| 4,543,955 | 10/1985 | Schroeppel | 604/66 X |
| 4,718,430 | 1/1988 | Holzer . | |
| 4,731,051 | 3/1988 | Fischell | 604/67 |
| 4,987,897 | 1/1991 | Funke | 607/32 |
| 5,233,386 | 8/1993 | Terashita | 355/41 |

FOREIGN PATENT DOCUMENTS

| | | |
|---|---|---|
| 0183351 | 6/1986 | European Pat. Off. . |
| 0317986 | 5/1989 | European Pat. Off. . |

OTHER PUBLICATIONS

"An Implantable Artificial Pancreas," Schubert et al., Med. & Biol. Eng. & Comput., vol. 18, (1980), pp. 527–537.

*Primary Examiner*—Randall L. Green
*Assistant Examiner*—Anh-Tuan T. Nguyen
*Attorney, Agent, or Firm*—Hill, Steadman & Simpson

[57]   ABSTRACT

A system for infusing medicine into the body of a patient includes an implantable infusion apparatus containing a dosing unit with a reservoir for the medicine and a medicine delivery pump for pumping doses of the medicine from the reservoir into the patient. The infusion apparatus also includes a sensor for sensing a parameter of the patient for controlling the dosing of medicine according to the sensed parameter. The dosing unit and the sensor are galvanically separable and are each provided with separate telemetry communication units for communication with an external programmer/controller. The external programmer/controller includes telemetry communication units for selectable communication with the dosing unit or the sensor or both simultaneously. The telemetry communication units of the external programmer/controller, the dosing unit and the sensor are constructed for bi-directional communication between the external controller and each one of the dosing unit and the sensor.

15 Claims, 1 Drawing Sheet

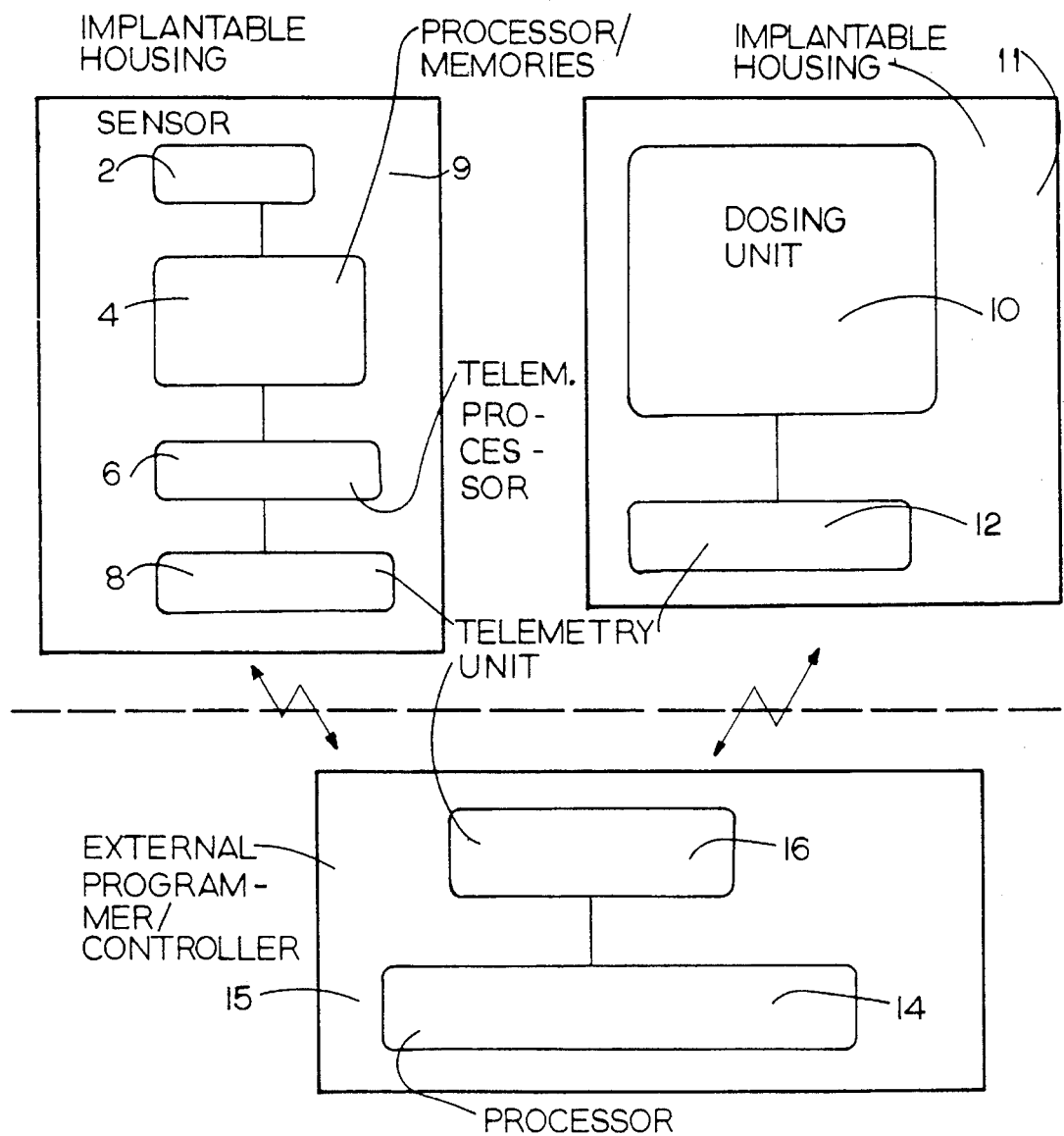

SYSTEM FOR INFUSION OF MEDICINE INTO THE BODY OF A PATIENT

BACKGROUND OF THE INVENTION

1. Field of the Invention

The present invention relates to a system for infusion of medicine into the body of a patient of the type including an implantable infusion apparatus containing a dosing unit with a reservoir for the medicine and a medicine delivery pump for pumping doses of medicine from the reservoir into the patient, a sensor for sensing a parameter of the patient for controlling the dosing of medicine according to the sensed parameter, the dosing unit and the sensor being galvanically separable (i.e. no direct path for electric current flow) and each being provided with separate telemetering communication means for communication with an external controller.

2. Description of the Prior Art

Systems of this type for infusion of, e.g., insulin are known, see e.g. U.S. Pat. No. 4,494,950 and W. Schubert et al, "An implantable artificial pancreas", Medical and Biological Engineering & Computing, 1980, 18, pp. 527–537. In the latter document an artificial implantable pancreas is described in which, in a first mode of operation, a glucose sensor transmits the actual blood glucose level to a control unit, in which the amount of insulin to be infused is calculated on the basis of patient specific parameters, recorded in a program memory and corresponding control signals for a dosing unit are determined by a control algorithm. If no sensor is used or if the sensor employed fails the dosing unit is controlled, in a second mode of operation, by a stored dosing program. Thus, the first mode of operation corresponds to a closed control loop and the second mode of operation to an open control loop.

In U.S. Pat. No. 4,543,955 a system is also described having an implantable physiological sensor for controlling an implantable device in response to changes in the parameter sensed by the sensor. The implantable device can be a heart pacing device, a drug infusion pump or another device interacting with a human body. In this system the sensor directly communicates with the device by conductors or a telemetry link. A heart pacing system of this type is also described in European Application 0,317,986.

Considerable efforts have been made in developing implantable closed loop systems for the control of blood glucose in which a sensor continuously monitors the glucose level and optimally controls the infusion of insulin into the patient. The creation of such an implanted system, which is completely safe to the patient, however, still poses significant difficulties.

SUMMARY OF THE INVENTION

An object of the present invention is to provide a new system for infusing medicine into the body of a patient in which the difficulties related to the above mentioned systems are avoided.

The above object is achieved in accordance with the principles of the present invention in a medication infusion system having a dosing unit with a reservoir for medication and a medication delivery pump connected to a catheter for pumping doses of the medication from the reservoir into the patient, a sensor which senses a physiological parameter of the patient for controlling the dosing of the medication according to the sensed parameter, and an external programmer/controller. The sensor and the dosing unit are both implanted in a patient, and each contain respective telemetry units which bi-directionally communicate with a telemetry unit in the external programmer/controller.

With the system according to the invention several important advantages are obtained. The operation of the sensor and the dosing unit can be easily checked individually. The sensor can easily be disconnected if it should fail and the dosing unit can be operated according to a dosing program or by manual control. The initial adjustment and calibration of the system and the development of an algorithm for controlling the dosing in response to the sensed parameter Can be easily performed by analyzing sensor data and selecting the dosing of medicine correspondingly. The system according to the invention is particularly well-suited for determining an algorithm from the sensor data at the beginning of the operation of the system, since the physician and/or the patient can easily change the initially-set control parameters and can adapt the insulin dosing to the sensed data according to experience, so that the first "approximation" is successively improved and adapted to the real needs of the patient based on the reaction of the body of the patient. It is also easy for the physician or the patient to intervene and change the control parameters later on. Further, because the functioning of the sensor and the dosing unit can be easily checked, reliable functioning of the system as a whole can be easily guaranteed.

The external controller of the system according to the invention further includes telemetry communication means for selectable communication with the dosing unit or the Sensor, or both simultaneously. In this way data can be received from the sensor and the dosing unit separately and an infusion schedule can be determined based on telemetered sensor data and telemetered dosing unit data.

Moreover in the system according to the invention the telemetry communication means of the external controller, the dosing unit and the sensor are constructed for two-way communication between the external controller and each one of the dosing unit and the sensor. In this way program data can be transferred from the external controller to the sensor and sensed data and calibration data can be delivered by the sensor to the external controller. Further, the dosing unit can receive infusion schedule data, safety related data, and system-indicating data and it can deliver patient related data, operation data of the dosing unit, and infusion reports to the external controller.

According to another embodiment of the system of the invention, the dosing unit and the sensor are mechanically separated. The dosing unit and the sensor can then be implanted at different times and at different sites in the body of the patient. In certain applications it is desirable to measure the relevant parameter in one point of the body and infuse the medicine in another.

According to another embodiment of the system of the invention, the external controller can be portably carried by the patient. This permits continuous communication link between the dosing unit and the sensor to be maintained by means the external controller, and according to a further version of this embodiment the dosing can be automatically controlled by the sensor. Thus, a closed control loop regulation is created.

According to another embodiment of the system of the invention the sensor is switchable by the external controller between a passive state and an active state, the sensor performing its functions in the active state. In this way the power consumption of the sensor is reduced.

In further embodiments of the system of the invention, the external controller can calculate an infusion schedule for the dosing unit from data received from the sensor and possibly also from the dosing unit. This calculation can be done in different ways, such as according to a stored algorithm or computer program, using a fuzzy logic system, or using a neural network system. The external controller can also include means for proposing to the patient a new or amended infusion schedule for acceptance or modification by the patient before being transmitted as the controlling infusion schedule to the dosing unit.

According to another embodiment of the invention, the external controller includes means for indicating information to the patient received from the sensor and the dosing unit. Such indicating means could be a display, a beeper, etc.

DESCRIPTION OF THE DRAWINGS

The single FIGURE is a schematic block diagram of a medication infusion system constructed in accordance with the principles of the present invention.

DESCRIPTION OF THE PREFERRED EMBODIMENTS

In the drawing an embodiment of the system according to the invention is shown, which includes an implantable sensor 2 with an associated data processor and memories 4, a telemetry processor 6 and telemetry communication unit 8. The system further includes an implantable dosing unit 10 containing a reservoir for the medicine to be infused into the body of a patient and a medicine delivery pump connected to a catheter having a tip located at an infusion site for pumping doses of the medicine from the reservoir into the patient. The dosing unit 10 further includes electronics for the control of its function and a power source, in the form of a battery, for its operation. These individual parts of the dosing unit 10 are not shown separately in the drawing because they are well-known to those skilled in the art and do not per se form any part of the invention.

The dosing unit 10 is also provided with a telemetry communication unit 12.

The sensor 2, the processor and memories 4, the telemetry processor 6 and the telemetry unit 8 are contained in an implantable housing 9, and the dosing unit 10 and the telemetry unit 12 are contained in another implantable housing 11. As indicated by the straight dashed line, the housings 9 and 11, and the components respectively contained therein, are implanted in a patient to whom the medication is to be administered.

The system further includes an external programmer/controller 15 containing a processor 14 with an associated telemetry communication unit 16 for bi-directional communication with the sensor 2 and its processor and memories 4 and telemetry processing 6, and the dosing unit 10, via their respective telemetry communication units 8 and 12.

The telemetry communication units 8, 12 and 16, of the sensor 2, the dosing unit 10, and the external programmer/controller 15 are each provided with sending and receiving circuitry for bi-directional communication between the processor 14 and each of the dosing unit 10 and the sensor 2.

The sensor 2 can be an insulin sensor which senses the blood sugar level of the patient. The sensed data can be transmitted continuously to the processor 14 of the external programmer/controller 15 which then controls the dosing unit 10 to deliver insulin accordingly.

The data sensed by the sensor 2 can also be stored in a memory in the processor and memories 4 and read out on command from the external programmer/controller 15. The sensor 2 can also deliver calibration data to the processor 14 of the external programmer/controller 15.

The sensor 2 can also receive program data from the processor 14 for storage in a memory of the processor and memories 4.

The sensor 2 is switchable by the processor 14, via the telemetry link, between an active state in which the parameter of interest is sensed, such as the blood sugar level, and in which information is received and sent to the processor 14, and a passive state in which the energy consumption is a minimum. In this way the total power consumption of the implant is reduced.

The dosing unit 10 is also switchable by the processor 14 between an active state and a low energy-consuming passive state. In its active state the dosing of insulin is performed and information is sent to and received from the processor 14 via the telemetry communication units 12 and 16. Thus, the dosing unit 10 can receive e.g., infusion schedule data from the processor 14. It can also receive and send safety related data, patient related data, operation data, and system identification data. Further, reports of successful infusions of insulin can be delivered from the dosing unit 10 to the processor 14 for comparison with predetermined limiting values so that the controlling of the dosing unit 10 can be changed when such a limiting value is reached. The dosing unit 10 is also able to confirm receipt of instructions from the processor 14 for safety reasons.

The external programmer/controller 15 contains (not shown) data entry means, user informing means, such as a display or beeper for providing information to the person in whom the other units are implanted, communication means and data storage means, all connected to the processor 14. The programmer/controller 15 can thus be operated to selectively activate the sensor 2 and the dosing unit 10 for receiving and sending information as described above and in a processor, can calculate infusion schedules based on telemetered sensor data according to a stored algorithm, a computer program or by means of a fuzzy logic system or a neural network system.

The infusion schedule can be based on telemetered sensor data and telemetered pump data from the dosing unit 10, or be calculated based on data received from the sensor 2 and a programmed patient dosing plan.

The external programmer/controller 15 also has means such as switches, buttons, microphones, etc (not shown) connected to the processor 14 for receiving information from the patient, and can be provided with means for sending and receiving data from other external apparatus such as an external computer.

As mentioned above, the dosing unit 10 can be automatically controlled by the external programmer/controller 15 in accordance with data received from the sensor 2 in a closed-loop regulation. The external programmer/controller 15 is then always carried by the patient, the programmer/controller 15 having a size and shape making it portable. The sensor 2 can, however, be disengaged from such closed loop control by the external programmer/controller 15 and the dosing unit 10 can be controlled manually or according to a predetermined dosing back-up program. This is of value if the sensor 2 should fail or other problems with the sensor circuit should appear.

The system according to the invention can also be provided with means for direct communication between the sensor 2 and the dosing unit 10, either telemetry communication means (as indicated by the dashed double arrow) or a galvanic (wired) connection. The system is then switchable between one mode of operation with direct communication between the sensor 2 and the dosing unit 10 and another mode of operation in which this direct connection is interrupted and communication between sensor 2 and dosing unit 10 takes place through the external programmer/controller 15.

The above embodiments of the system according to the invention have been described for insulin therapy, however, the system according to the invention can be used for infusion of other kinds of medicines. Thus, the system according to the invention can be used for, e.g. patient's subject to abnormal blood pressure or patients having circulatory disorders for providing such persons with medicine. The sensor 2 is then a sensor for sensing blood pressure or a peripherally implanted oxygen sensor.

Although modifications and changes may be suggested by those skilled in the art, it is the intention of the inventors to embody within the patent warranted hereon all changes and modifications as reasonably and properly come within the scope of their contribution to the art.

We claim as our invention:

1. In a system for infusing medication into the body of a patient having an implantable infusion apparatus containing a dosing unit with a reservoir for medication and a pump for pumping doses of said medication from said reservoir into the patient, a sensor for sensing a physiological parameter of the patient for use in controlling the dosing of medication, dependent on said sensed parameter, and an external programmer/controller, the improvement comprising:

said sensor and said dosing unit having no galvanic connection therebetween;

first telemetry means implanted with and connected to said sensor, for bi-directional telemetry communication with said programmer/controller for transmitting data, at least comprising said sensed parameter, to, and for receiving data and instructions from, said programmer/controller;

second telemetry means implanted with and connected to said dosing unit, for bi-directional telemetry communication with said programmer/controller for transmitting data to, and receiving data and instructions from, said programmer/controller;

third telemetry means, disposed in said programmer/controller, for bi-directional telemetry communication with each of said first and second telemetry means, and means for selectively establishing said bi-directional communication with said first and second telemetry means individually or simultaneously; and said first, second and third telemetry means comprising, in combination, means for closed-loop telemetric control of the delivery of medication to said patient by communication between said sensor and said dosing unit via said programmer controller.

2. A system as claimed in claim 1 further comprising a first implantable housing containing said sensor and said first telemetry means and a second implantable housing, separated from said first implantable housing, containing said dosing unit and said second telemetry means.

3. A system as claimed in claim 1 wherein said programmer/controller comprises a housing having a size and shape for portable carrying of said programmer/controller by said patient.

4. A system as claimed in claim 1 wherein said first telemetry means further comprises means for telemetric communication with said second telemetry means, and wherein said second telemetry means comprises means for telemetric communication with said first telemetry means forming an additional closed-loop telemetric control of the delivery of medication to said patient redundant to said means for closed-loop telemetric control.

5. A system as claimed in claim 1 wherein said sensor is operable in an active, power-consuming state during which time said parameter is sensed, and a passive, non-power consuming state, and wherein said programmer/controller comprises means for selectively switching said sensor between said active state and said passive state.

6. A system as claimed in claim 1 wherein said sensor comprises memory means for storing said data relating to said parameter, and wherein said programmer/controller comprises means for selectively reading out said data via said first and third telemetry means.

7. A system as claimed in claim 1 wherein said programmer/controller comprises means for calculating and infusion schedule from said data relating to said sensed parameter and for transmitting said infusion schedule to said dosing unit via said third and second telemetry means for operating said dosing unit according to said infusion schedule.

8. A system as claimed in claim 7 wherein said programmer/controller comprises means for informing said patient of a new infusion schedule based on said data relating to said sensed parameter, and means for permitting said patient to selectively accept or modify said new infusion schedule before said new infusion schedule is telemetered to said second telemetry means from said third means.

9. A system as claimed in claim 1 wherein said programmer/controller comprises means for storing a programmed patient dosing plan and means for calculating an infusion schedule dependent on said data relating to said sensed parameter received from said sensor via said first and third telemetry means and said programmed patient dosing plan, and for transmitting said infusion schedule to said dosing unit via said third and second telemetry means for operating said dosing unit to deliver said medication according to said infusion schedule.

10. A system as claimed in claim 1 wherein said programmer/controller comprises means for calculating an infusion schedule from said data received from said sensor relating to sensed parameter and said data received from said dosing unit, and for transmitting said infusion schedule to said dosing unit via said third and second telemetry means for operating said dosing unit to deliver said medication according to said infusion schedule.

11. A system as claimed in claim 1 wherein said programmer/controller means comprises means for informing said patient of said data relating to said sensed parameter received from said sensor and said data received from said dosing unit.

12. A system as claimed in claim 1 wherein said programmer/controller comprises means for storing an algorithm and for calculating an infusion schedule based on said algorithm, and for transmitting said infusion schedule to said dosing unit via said third and second telemetry means for operating said dosing unit according to said infusion schedule.

13. A system as claimed in claim 1 wherein said programmer/controller comprises means for storing a computer program and for calculating an infusion schedule based on said computer program, and for transmitting said infusion schedule to said dosing unit via said third and second telemetry means for operating said dosing unit according to said infusion schedule.

14. A system as claimed in claim 1 wherein said programmer/controller comprises fuzzy logic means for calculating an infusion schedule, and means for transmitting said infusion schedule to said dosing unit via said third and second telemetry means for operating said dosing unit according to said infusion schedule.

15. A system as claimed in claim 1 wherein said programmer/controller comprises neural network means for calculating an infusion schedule, and means for transmitting said infusion schedule to said dosing unit via said third and second telemetry means for operating said dosing unit according to said infusion schedule.

* * * * *